United States Patent [19]

Keith et al.

[11] Patent Number: 4,764,378
[45] Date of Patent: Aug. 16, 1988

[54] BUCCAL DRUG DOSAGE FORM

[75] Inventors: Alec D. Keith, Boalsburg; Wallace C. Snipes, Pine Grove Mills, both of Pa.

[73] Assignee: Zetachron, Inc., State College, Pa.

[21] Appl. No.: 827,615

[22] Filed: Feb. 10, 1986

[51] Int. Cl.⁴ .......................... A61K 9/20; A61K 9/26; A61K 31/74; A61K 31/79

[52] U.S. Cl. .................................. 424/435; 424/78; 424/80; 424/81; 424/464; 424/486; 424/487

[58] Field of Search ................... 424/78, 80, 81, 435, 424/464, 486, 487

[56] References Cited

U.S. PATENT DOCUMENTS

| | | | |
|---|---|---|---|
| 2,698,822 | 1/1955 | Halpern et al. | 167/65 |
| 2,975,099 | 3/1961 | Goyan et al. | 167/64 |
| 3,039,933 | 6/1962 | Goldman | 167/82 |
| 3,429,308 | 2/1969 | Russell | 424/464 |
| 3,444,858 | 5/1969 | Russell | 424/464 |
| 3,511,914 | 5/1970 | Wolkoff | 424/263 |
| 3,536,809 | 10/1970 | Applezweig | 424/28 |
| 3,598,122 | 8/1971 | Zaffaroni | 128/268 |
| 3,634,584 | 1/1972 | Poole | 424/21 |
| 3,670,065 | 6/1972 | Eriksson et al. | 264/131 |
| 3,764,703 | 10/1973 | Bergström et al. | 424/319 |
| 3,767,789 | 10/1973 | Rankin | 424/78 |
| 3,832,460 | 8/1974 | Kosti | 424/54 |
| 3,870,790 | 3/1975 | Lowey et al. | 424/488 |
| 3,881,011 | 4/1975 | Amann | 424/270 |
| 3,911,099 | 10/1975 | DeFoney et al. | 424/28 |
| 3,972,995 | 8/1976 | Tsuk | 424/28 |
| 4,039,653 | 8/1977 | DeFoney et al. | 424/19 |
| 4,059,686 | 11/1977 | Tanaka | 424/81 |
| 4,104,190 | 8/1978 | Hartshorn | 252/187 R |
| 4,139,627 | 2/1979 | Lane et al. | 424/267 |
| 4,151,273 | 4/1979 | Riegelman et al. | 424/78 |
| 4,222,956 | 7/1980 | Dhabhar et al. | 523/120 |
| 4,226,848 | 10/1980 | Nagai et al. | 424/435 |
| 4,250,163 | 2/1981 | Nagai et al. | 424/14 |
| 4,250,169 | 2/1981 | Hosoi et al. | 424/181 |
| 4,264,573 | 4/1981 | Powell et al. | 424/19 |
| 4,280,936 | 7/1981 | Dhabhar et al. | 260/13 |
| 4,292,299 | 9/1981 | Suzuki et al. | 424/435 |
| 4,318,742 | 3/1982 | Lokken | 106/35 |
| 4,333,919 | 6/1982 | Kleber et al. | 424/15 |
| 4,474,902 | 10/1984 | Dhabhar et al. | 523/120 |
| 4,514,528 | 4/1985 | Dhabhar et al. | 523/120 |
| 4,517,173 | 5/1985 | Kizawa et al. | 424/435 |
| 4,518,721 | 5/1985 | Dhabhar et al. | 523/120 |
| 4,521,551 | 6/1985 | Chang et al. | 523/120 |
| 4,529,589 | 7/1985 | Davydov et al. | 424/435 |
| 4,530,942 | 7/1985 | Dhabhar et al. | 523/118 |
| 4,542,168 | 9/1985 | Chang et al. | 523/118 |
| 4,569,955 | 2/1986 | Dhabhar | 523/120 |
| 4,572,832 | 2/1986 | Kigasawa et al. | 424/435 |
| 4,624,849 | 11/1986 | Toogood | 424/78 |
| 4,629,621 | 12/1986 | Snipes | 424/19 |
| 4,713,239 | 12/1987 | Babaian et al. | 424/81 |

FOREIGN PATENT DOCUMENTS

| | | | |
|---|---|---|---|
| 59-181218 | 10/1984 | Japan | 424/435 |
| 8600802 | 2/1986 | World Int. Prop. O. | |
| 1063185 | 3/1967 | United Kingdom | |
| 1083896 | 9/1967 | United Kingdom | 424/435 |
| 1171691 | 11/1969 | United Kingdom | 424/435 |
| 2021610A | 12/1979 | United Kingdom | |
| 2108841A | 5/1983 | United Kingdom | 424/435 |

OTHER PUBLICATIONS

Brochure describing Polyox ® poly(ethylene oxide), Union Carbide Corp., 1981.
"Carbowax" ® polyethylene glycol brochure, Union Carbide Chemicals Co., 1960.

Primary Examiner—Shep K. Rose
Attorney, Agent, or Firm—Vorys, Sater, Seymour & Pease

[57] ABSTRACT

Buccal dosage forms for transmucosal administration of drugs comprise a pharmaceutical compound dispersed in an erodible matrix comprising from about 20 to about 75 percent by weight of a low molecular weight polyethylene glycol component, from about 2 to about 65 percent by weight of a medium or high molecular weight polyethylene glycol component, from about 1% to about 40% percent by weight of an auxiliary high molecular weight polymer.

Preferred auxiliary high molecular weight polymers are polyethylene oxide and polyvinylpyrrolidone which improve the molding properties of the matrix and provide water-activated adhesive properties to the compositions to provide a buccal dosage form.

45 Claims, No Drawings

BUCCAL DRUG DOSAGE FORM

BACKGROUND OF THE INVENTION

1. Field of the Invention

This invention relates to dosage forms for administration of drugs and more particularly to buccal dosage forms having a polymeric matrix for controlled release of a drug.

2. Description of the Prior Art

Administration of drugs by absorption through the oral mucosa has been found to be an efficient and convenient method of supplying to the body a drug which is not well adapted to administration via the intestinal route. Some drugs are poorly absorbed from the gastrointestinal tract; others are rapidly metabolized in the liver and do not reach the target organ. Transmucosal administration, which introduces the drug directly into the bloodstream, avoids the problems of poor absorption or rapid metabolism.

However, because the continuous secretion of saliva rapidly washes dissolved drugs out of the oral cavity, sublingual and buccal administration of drugs have been most useful for drugs, such as nitroglycerin, which are very rapidly absorbed through the oral mucosa. In order to keep a drug in contact with the oral mucosa for a longer period of time, sustained release dosage forms especially adapted for transmucosal administration of drugs have been developed. These have generally comprised a drug dispersed in a matrix which slowly releases the drug by diffusion from the matrix or by slow dissolution or erosion of the matrix. In order to retain the dosage form within the mouth, it may be bonded to an adhesive patch or the dosage form itself may be provided with an adhesive layer which adheres to the mucosa. Alternatively, the dosage form itself may adhere to the mucosa and slowly dissolve, releasing the drug contained therein.

For example, Zaffaroni, U.S. Pat. No. 3,598,122, discloses an adhesive buccal device having an impermeable backing layer and a drug-containing adhesive matrix layer which adheres to the oral mucosa, allowing the drug to diffuse through the mucosa over a period of time. This device has the drawback that it must be removed from the mouth after the drug has been dispensed.

Another adherent dosage form comprising an impervious backing material coated with an adhesive which adheres to the mucosa and having a drug reservoir matrix comprised of a mixture of low molecular weight polyethylene glycol and polyvinylpyrrolidone is disclosed in Tsuk, U.S. Pat. No. 3,972,995. Evidently this dosage form suffers from the same problems as that of Zaffaroni.

Another approach is exemplified by Nagai, U.S. Pat. No. 4,250,163, who discloses a totally soluble adhesive buccal dosage form which adheres to the oral mucosa and releases the medication over a period of 10–40 minutes. The dosage form is a lamella having the drug dispersed in a matrix comprised of 50–95% of a cellulose ether and 5–50% of an acrylic polymer. These dosage forms are prepared by compression molding of a mixture of ingredients in powder form, which sometimes presents problems in obtaining uniform distribution of the drug in the matrix.

A buccal dosage form comprising a strip of gauze or paper impregnated with a drug in a matrix of a mixture of polyethylene glycols is disclosed in Applezweig, U.S. Pat. No. 3,536,809. This dosage form also has the drawback that the supporting gauze or paper must be removed from the mouth after the medicine has been exhausted.

DeFoney, in U.S. Pat. Nos. 3,911,099 and 4,039,653, discloses a dosage form comprising a tablet or similar article formed of a sustained release matrix of polyvinylpyrrolidone containing an odor masking substance which is retained in the oral cavity by means of an adhesive layer on one side of the tablet.

Hence a need has continued to exist for a buccal dosage form which adheres to the oral mucosa, provides for administration of medication over a controlled period of time, has a very uniform distribution of the drug in the matrix, and which completely dissolves in the mouth.

SUMMARY OF THE INVENTION

In accordance with the present invention a matrix composition is provided into which a drug can be mixed while the matrix is in the molten state and which can then be injection molded into unit doses suitable for buccal administration. The composition comprises three essential ingredients in defined proportions as follows:

from about 20% to about 75% by weight of a low molecular weight polyethylene glycol component, from about 2% to about 65% by weight of a medium or high molecular weight polyethylene glycol component, and from about 1% to about 40% by weight of an auxiliary high molecular weight polymer.

A dosage form of the invention, particularly a buccal dosage form, comprises an effective amount of a transmucosally administered drug dispersed in the molded erodible matrix.

The dosage forms of the invention may include disks, wafers, tablets, lozenges, lamellae and the like.

Accordingly, it is an object of the invention to provide a buccal drug dosage form.

A further object is to provide a buccal dosage form having controlled release properties.

A further object is to provide an erodible matrix for a buccal dosage form which completely dissolves in the oral cavity.

A further object is to provide a buccal dosage form which adheres to the oral mucosa.

A further object is to provide a buccal dosage form which is easily manufactured.

A further object is to provide a buccal dosage form which can be manufactured by injection molding.

Further objects of the invention will become apparent from the description of the invention which follows.

DETAILED DESCRIPTION OF THE INVENTION AND PREFERRED EMBODIMENTS

The buccal dosage form of this invention is a blend of ingredients chosen to provide the proper physical properties in manufacture and use. The injection moldable matrix should have a melting point which is high enough to prevent fusion of packaged dosage forms during storage in a reasonably temperate environment, yet low enough to permit mixing of the active pharmaceutical ingredient with the molten matrix without causing significant decomposition of the pharmaceutical compound. The molten matrix should also have a viscosity suitable for mixing the active ingredient and for injection molding to form buccal dosage forms. The solidified buccal dosage form may also require special properties. For example, in some cases, it may be desirable for the buccal dosage form to adhere to the oral mucosa, so that it is retained in the oral cavity for a period of time while slowly releasing the active ingredient. While the compositions of the invention are specially adapted for use as buccal dosage forms, they may also be used as conventional oral dosage forms which are swallowed and deliver their medication via the gastrointestinal tract.

The desired combination of properties in the buccal dosage form of this invention is achieved by proper choice of the proportions of the three basic components of the matrix.

The first component of the buccal matrix of the invention is a low molecular weight polyethylene glycol (PEG) component which may be a single PEG or a mixture of low molecular weight PEG's. For purposes of this invention, low molecular weight PEG's are those having a molecular weight not greater than about 4000 daltons. The proportion of low molecular weight PEG component may range from about 20% to about 75% by weight of the matrix. The proportion of low molecular weight PEG component affects the rate at which the matrix is eroded by saliva and therefore the rate of release of the drug and the duration of its action. In general, greater amounts of low molecular weight PEG component increase the rate of erosion. The relative amounts of the low molecular weight PEG component and the medium or high molecular weight component determine the melting point of the buccal matrix of the invention. Mixtures of low molecular weight PEG's can be used to attain a desired average molecular weight and the desired effect on the properties of the matrix. A preferred low molecular weight PEG component comprises a mixture of PEG 1000, PEG 1450 and PEG 3350, where the numbers signify the molecular weight as is conventional. Another preferred low molecular weight PEG component comprises a mixture of PEG 1450 and PEG 3350.

The medium to high molecular weight polyethylene glycol component has a molecular weight in the range from about 6000 daltons to about 20,000 daltons, Its proportion in the matrix may range from about 2% to about 65% by weight. Greater amounts of the medium to high molecular weight component tend to increase the melting point of the mixture, and favor the noncrystalline character of the matrix.

The viscosity of the molten material should be low enough to provide for easy mixing of the active ingredient into the matrix and also for conforming to the final molded shape. This includes the ability to flow freely into thin layers when lamellae or disks are to be prepared by casting, and the ability to flow freely through the sprues of a multiple form injection mold.

The buccal dosage form matrix should also be nonhygroscopic for ease in handling the dosage forms and should have good mold-release properties to facilitate manufacture by injection molding.

The third ingredient of the buccal dosage matrix of the invention is a high molecular weight polymer introduced to adjust the properties of the matrix, particularly the melt viscosity and the molding properties of the molten matrix and the adhesion of the dosage form to the oral mucosa. The proportion of the third ingredient ranges from about 1% to about 40% by weight of the matrix. Suitable high molecular weight polymers include polyvinylpyrrolidone (PVP), polyethylene oxide (PEO), poly(acrylic acid) (PAA), sodium alginate and carboxymethyl cellulose. Preferred high molecular weight polymers include polyvinylpyrrolidone and polyethylene oxide. Both of these polymers provide the matrix with water-activated adhesive properties for good adhesion to the oral mucosa. They also influence the melt viscosity of the molten matrix. The PEO used in the matrix may have a molecular weight from about 100,000 to about 5,000,000 daltons. The PVP may have a molecular weight from about 30,000 to about 90,000 daltons.

In a preferred matrix of the invention the auxiliary polymeric ingredient is polyvinylpyrrolidone in a proportion of about 25% to about 40% by weight of the matrix. This dosage form rapidly disintegrates and dissolves after being placed in the buccal pouch, in a period of about 60 seconds, leaving no noticeable residue, but rather a coating of the matrix ingredients which adhere to a relatively large area of the mucosa surrounding the site where the dosage form was placed. The presence of this thin coating is unnoticeable to the patient, but it continues to dispense the drug through the mucosa until such time as the drug is used up or the matrix dissolves in the mouth fluids. Thus, the drug is typically dispensed over a period of 10–30 minutes via transmucosal absorption directly into the bloodstream.

Additional ingredients in minor amounts may be incorporated into the buccal matrix of the invention to provide desirable physical properties or modify the properties of the matrix. For example, a plasticizer such as propylene glycol, may be added in amounts up to about 5% by weight of the matrix.

The buccal dosage form of the invention is prepared by mixing the ingredients at a temperature such that the PEG's are molten and can serve as a solvent for the auxiliary high molecular weight polymeric ingredients, for any additional auxiliary ingredients and for the active pharmaceutical ingredient. In general, the PEG's are melted and mixed in a vessel equipped with a stirrer and a heating device, such as a heating mantle or steam jacket. Such melting usually occurs at about 60°–80° C. and the viscosity and plasticity adjusting ingredients, e.g., polyethylene oxide or polyvinylpyrrolidone, any auxiliary ingredients and the pharmaceutically active ingredient are added while stirring. After the blending is complete, buccal dosage forms are prepared by conventional procedures, such as casting a thin layer of the composition on a flat surface, allowing it to harden and cutting the layer so prepared into dosage forms, or by injection molding.

Formulation of the compositions of the invention in the molten state has a number of advantages over the conventional method of formulation by mixing of powdered or granulated ingredients in the solid state. The mixing equipment needed for mixing of liquid ingredients is generally simpler than that used for solid materials. The fact that the ingredients are actually dissolved in the matrix makes for more uniform distribution of the active ingredients in the composition and a more uniform rate of release as the dosage form dissolves in the oral cavity. The use of a molten matrix for formulating the composition also permits the use of injection molding to prepare the dosage forms themselves.

Injection molding of pharmaceutical dosage forms has a number of advantages over conventional tabletting. Injection molding allows a greater uniformity in size and density, a greater range of shapes for the dosage forms, and a greater uniformity of distribution of the drug within the matrix. Handling and metering of a molten matrix composition is also much simpler than for powdered or granulated compositions.

Any drug suitable for transmucosal administration may be incorporated into the buccal dosage form of this invention. Such drugs may include locally or systemically acting drugs, but in most cases will be systemically acting drugs. The drugs may be selected from among any group wherein a transmucosal administration of the drug over a period ranging from a few minutes to several minutes is desired. The drug may be selected from among analgesic, anorexic, antiarthritic, antibacterial, antibiotic, anticonvulsant, anti-depressant, antidiabetic, antifungal, antihistaminic, anti-hypertensive, anti-inflammatory, anti-neoplastic, antiparkinsonism, antipyretic, anticholinergic, anesthetic, antimicrobial, antiviral, anti-ulcer, bronchodilator, cardiovascular, contraceptive, central nervous system affecting, inotropic, vasodilator, vasoconstrictor, decongestant, diuretic, hypoglycemic, hormone, hypnotic, hematinic, electrolyte supplement, germicidal, muscle relaxant, parasympatholytic, parasympathetomimetic, tranquilizer, ophthalmic, psychostimulant, vitamin, and the like drugs.

Preferred drugs for incorporation into the buccal dosage form of this invention include estrogens in general, e.g. estradiol and esters thereof such as the valerate ester, ethinylestradiol, progestins including norethindrin, gonadotropin releasing hormone (GNRH), human growth hormone, insulin, nicotine, phenylephrine, desmopressin (DDAVP), oxytocin, vasopressin, epinephrine, peptides useful in the treatment of patients with Paget's disease or other calcium deficiency syndromes, such as calcitonin and the like, nitroglycerin, isosorbide dinitrate, scopolamine, verapamil, oxymetazoline, tamoxifen and the like.

The proportion of active ingredient in the buccal dosage form of the invention will vary according to the potency of the drug and the needs of the patient, as will be understood by those skilled in the art. The active ingredient will generally comprise from about 0.01 percent by weight to about 10 percent by weight, typically 0.1 percent to 1 percent by weight, the remainder of the composition being the matrix. The concentration of the drug in the composition will also vary with the size of the dosage form prepared, since as will be understood by those skilled in the art, the amount of drug delivered in a single dose will depend on both the concentration of the drug in the matrix and the size of the buccal dosage form.

A particularly preferred buccal dosage form of the invention incorporates an estrogen, a progestin or preferably both, to prepare a dosage form useful as an oral contraceptive or a post-menopausal estrogen supplement. An oral contraceptive dosage form according to the invention will typically contain a progestin and an estrogen in amounts suitable for providing contraceptive activity. A typical contraceptive formulation will include 0.02–0.05 percent by weight of ethinylestradiol and 1.0–5.0 percent by weight of norethindrone in a buccal matrix of the invention. A typical dosage form for post-menopausal estrogen supplement will contain 0.2–0.5 percent by weight of 17-beta-estradiol and 1.0–5.0 percent by weight of norethindrone in a buccal matrix of the invention.

The buccal dosage forms prepared from the composition of this invention may have any of the conventional shapes and sizes used for such dosage forms. For example a dosage form may be in the form of a lozenge, a lamella, a disk, a wafer, a tablet or the like. It should have dimensions which fit conveniently into the buccal cavity or under the tongue. Suitable dimensions for the dosage form are a length of 5 to 10 mm, a width of 2 to 10 mm and a thickness of 0.2 to 3 mm. A preferred thickness is 0.5 to 1.5 mm. The total weight of the dosage form may be from about 10 to about 150 mg, preferably 50 to 100 mg.

The invention will be illustrated by the following examples, which are not intended to be limiting. Parts and percentages in the examples are by weight unless otherwise specified.

EXAMPLE 1

This example illustrates the preparation of a buccal dosage form of the invention.

A molten mixture was prepared by the procedure described above having the following composition

| PEG 1000 | 20% |
|---|---|
| PEG 1450 | 38% |
| PEG 3350 | 3% |
| PEG 8000 | 3% |
| Propylene glycol | 3% |
| Polyvinylpyrrolidone | 33% |

After the ingredients were melted together, the molten mixture was cast on a smooth flat surface and allowed to cool. The film so formed was hard and somewhat flexible at room temperature. Dosage forms of a size to fit comfortably in the buccal pouch were cut from the film (about 1 cm×3 cm). These lamellae dissolved rapidly when placed in the buccal pouch or sublingually.

Another dosage form was prepared by the same procedure except that a small amount of a dye was incorporated into the matrix. When the dosage form was placed in the buccal pouch, it dissolved in less than 60 seconds. However, it was observed from the dye pattern that the matrix adhered to an area of about 10 cm² on the cheek and about 10 cm² on the adjacent gum, and remained there for a period of 10–30 minutes.

EXAMPLE 2

This example illustrates another formulation of a dosage form of this invention.

A molten mixture was prepared by the procedure described above having the following composition

| PEG 1000 | 18% |
|---|---|
| PEG 1450 | 38% |
| PEG 3350 | 3% |
| PEG 8000 | 3% |
| Propylene glycol | 5% |
| Polyvinylpyrrolidone | 33% |

When tested by the procedure of Example 1, this formulation also was found to dissolve rapidly and to form a coating on the mucosa close to the site of application.

EXAMPLE 3

A 10 g batch of the composition of Example 1 was prepared incorporating 20 mg of scopolamine. The formulation was molded by injection molding to prepare a buccal dosage form containing 0.2% of scopolamine useful for treating patients having motion sickness.

EXAMPLE 4

A 10 g batch of the composition of Example 1 was prepared incorporating 5% by weight of verapamil hydrochloride to prepare a buccal dosage form useful for treating cardiovascular conditions.

EXAMPLE 5

This example illustrates a buccal matrix composition of the invention.

By the general procedure outlined above a number of matrix formulations were prepared having the following compositions:

|  | A | B | C | D |
|---|---|---|---|---|
| PEG 1000 | 71% | 60% | 60% | 61% |
| PEG 20,000 | 11% | 15% | 20% | 22% |
| PEO (MW 100,000) | 18% | 25% | 20% | 17% |

In general all formulations exhibited satisfactory rates of erosion when used as buccal dosage forms.

A quantity of 20 mg of calcitonin was added to 10 g of the molten composition A and a buccal dosage form was prepared containing 0.2% of calcitonin which was useful in treating patients with Paget's disease or other calcium deficiency syndromes.

A quantity of 10 mg of scopolamine was added to 10 g of the molten composition A to form a pharmaceutical composition which was formed into a buccal dosage forms containing 0.1% scopolamine useful in treating patients having motion sickness.

Verapamil hydrochloride was mixed with the molten composition C in an amount equal to 5% of the total composition, and the molten composition was molded into buccal dosage forms useful in treating patients having cardiac arrythmia or angina pectoris.

Verapamil (free base) was mixed with the molten composition D in an amount equal to 10% of the total composition. The composition was formed into buccal dosage forms useful for transmucosal administration of verapamil for treating cardiovascular conditions.

EXAMPLES 6–10

The examples illustrate dosage forms according to the invention incorporating other drugs.

An excipient composition is prepared having the composition of Example 5A. To separate portions of the composition are added amounts of the gonadotropin releasing hormone (GNRH), insulin, phenylephrine, desmopressin (DDAVP) and epinephrine to prepare pharmaceutical compositions containing effective amounts of each drug. Buccal dosage forms are prepared which are useful in treating patients in need of these drugs.

EXAMPLE 11

This example illustrates the effect of varying proportions of polyethylene oxide on the buccal controlled release matrices of the invention.

By the general procedure outlined above a series of matrix formulations were prepared having the following compositions

|  | A | B | C | D |
|---|---|---|---|---|
| PEG 3350 | 49.0% | 48.0% | 46.3% | 43.1% |
| PEG 8000 | 19.6% | 19.4% | 18.6% | 17.2% |
| PEG 20000 | 29.4% | 28.8% | 27.7% | 25.9% |
| PEO (MW 100,000) | 2.0% | 3.8% | 7.4% | 13.8% |

Formulations A and B exhibited good viscosity characteristics for mixing in a pharmaceutical compound; formulation C was acceptable; formulation D was difficult to use at 80° C. because it exhibited a relatively high viscosity and stringiness.

EXAMPLE 12

This example illustrates another buccal device of the invention.

A formulation was prepared by the general procedure described above having the following composition:

| PEG 3350 | 44.9% |
|---|---|
| PEG 8000 | 20.0% |
| PEG 20000 | 30.0% |
| PEO (MW 100,000) | 5.0% |
| Scopolamine HCl | 0.1% |

A buccal device was made from this composition which was useful in administration of scopolamine to patients suffering from motion sickness.

EXAMPLE 13

This example illustrates another buccal matrix of this invention.

A formulation was prepared by the general procedure described above having the following composition:

| PEG 1000 | 50.0% |
|---|---|
| PEG 8000 | 24.9% |
| PEO (MW 5,000,000) | 0.1% |
| PVP (MW 30,000) | 20.0% |
| PVP (MW 90,000) | 5.0% |

This matrix was easy to mold but was somewhat hygroscopic.

EXAMPLE 14

This example illustrates another buccal matrix of the invention.

A formulation was prepared by the general procedure described above having the following composition:

| PEG 1000 | 24% |
|---|---|
| PEG 1450 | 20% |
| PEG 3350 | 10% |
| PEG 8000 | 10% |
| Propylene glycol | 3% |
| PVP (MW 30,000) | 33% |

This composition yielded a solid matrix which rapidly dissolved in water but was somewhat hygroscopic.

EXAMPLE 15

This example illustrates another buccal matrix of the invention.

A formulation was prepared by the general procedure described above having the following composition:

| | |
|---|---|
| PEG 1000 | 18% |
| PEG 1450 | 38% |
| PEG 3350 | 3% |
| PEG 8000 | 3% |
| Propylene glycol | 5% |
| PVP (MW 30,000) | 33% |

EXAMPLE 16

This example illustrates another buccal matrix of the invention.

A formulation was prepared by the general procedure described above having the following composition:

| | |
|---|---|
| PEG 1000 | 20% |
| PEG 1450 | 10% |
| PEG 3350 | 58% |
| PEG 8000 | 9% |
| Propylene glycol | 2% |
| PEO (MW 5,000,000) | 1% |

EXAMPLE 17

This example illustrates another buccal dosage form of the invention.

A formulation was prepared by the general procedure described above having the following composition:

| | |
|---|---|
| PEG 3350 | 30.0% |
| PEG 8000 | 64.8% |
| PEO (MW 5,000,000) | 5.0% |
| Calcitonin | 0.2% |

This composition exhibited excellent physical properties and could be easily molded into buccal dosage forms by injection molding.

EXAMPLE 18

This example illustrates another buccal matrix of the invention.

A formulation was prepared by the general procedure described above having the following composition:

| | |
|---|---|
| PEG 1450 | 11.0% |
| PEG 3350 | 25.4% |
| PEG 8000 | 60.6% |
| PEO (MW 5,000,000) | 3.0% |

This formulation was used to prepare buccal dosage forms which dissolved slightly faster than those of Example 17.

EXAMPLE 19

This example illustrates a highly preferred buccal matrix of the invention.

A formulation was prepared by the general procedure described above having the following composition:

| | |
|---|---|
| PEG 1450 | 11.0% |
| PEG 3350 | 25.0% |
| PEG 8000 | 59.0% |
| PEO (MW 5,000,000) | 5.0% |

EXAMPLE 20

This example illustrates the preparation of dosage forms suitable for use as oral contraceptives or postmenopausal estrogen supplements.

A buccal dosage form matrix having the following composition is prepared by the procedure of Example 1.

| | |
|---|---|
| PEG 1000 | 20% |
| PEG 1450 | 34% |
| PEG 3350 | 8% |
| PEG 8000 | 5% |
| Propylene glycol | 3% |
| PVP (MW 30,000) | 30% |

Into portions of this matrix are incorporated the following estrogens and progestins in the listed proportions

| | | |
|---|---|---|
| A. | 17-beta-estradiol | 0.2% by weight |
| B. | ethinylestradiol | 0.02% by weight |
| C. | norethindrone | 2.0% by weight |
| D. | ethinylestradiol | 0.02% by weight |
| | norethindrone | 2.0% by weight |
| E. | 17-beta-estradiol | 0.2% by weight |
| | norethindrone | 2.0% by weight |

Formulation A through C are useful as components of a dosage regimen for contraception or estrogen supplement. Formulation D is suitable for use as an oral contraceptive. Formulation E is suitable as a postmenopausal estrogen supplement.

EXAMPLE 21

This example illustrates the superior bioavailability provided by transmucosal administration using the buccal dosage forms of this invention as compared with oral administration.

A buccal dosage form matrix having the following composition was prepared by the procedure of Example 1.

| | |
|---|---|
| PEG 1000 | 20% |
| PEG 1450 | 34% |
| PEG 3350 | 8% |
| PEG 8000 | 5% |
| Propylene glycol | 3% |
| PVP (MW 30,000) | 30% |

Dosage forms were prepared from this matrix in the form of lozenges containing 192 micrograms of 17-beta-estradiol each. The dosage forms were administered to a human volunteer by the buccal route (transmucosal absorption) and by the oral route (absorption from the gastrointestinal tract). Blood levels were measured at various intervals after administration and the results for each method of administration are given below.

| Time after administration (minutes) | Plasma level (micrograms/milliliter) |
|---|---|
| Oral administration | |
| 0 | 10 |
| 30 | 89 |
| 90 | 64 |
| 240 | 94 |
| 360 | 10 |
| Buccal Administration | |
| 0 | 15 |
| 30 | 655 |
| 90 | 355 |
| 240 | 115 |
| 360 | 18 |

Inspection of the data reveals that the blood level attained via buccal administration is much greater than that attained by oral administration.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

What is claimed is:

1. An injection molded, cast, or otherwise solidified buccal or transmucosal oral mucosa adherent dosage form having dimensions which fit into the buccal cavity or under the tongue of a user thereof comprising a pharmaceutical ingredient selected from a pharmaceutical compound, a pharmaceutically acceptable salt, and derivatives thereof adapted to be dispensed typically over a period of 10–30 minutes through transmucosal absorption directly into the bloodstream, said pharmaceutical ingredient being dispersed in a non-crystalline, solidified polymeric matrix which adheres to oral mucosa after being activated by water or saliva comprising, from about 20 to about 75 percent by weight of a polyethylene glycol component having a low molecular weight of from about 100–4000,
   from about 2 to about 54 percent by weight of a polyethylene glycol component having a medium to high molecular weight of from about 6000–20,000, and
   from about 1 to about 40 percent by weight of polyethylene oxide having a high molecular weight of from about 100,000 to 5,000,000.

2. The dosage form of claim 1 wherein said low molecular weight polyethylene glycol component is a mixture of low molecular weight polyethylene glycols.

3. The dosage form of claim 2 wherein said mixture of low molecular weight polyethylene glycols comprises PEG 1000, PEG 1450 and PEG 3350.

4. The dosage form of claim 1 wherein said low molecular weight polyethylene glycol component is present in a proportion of from about 35% to about 65% by weight of the total composition.

5. The dosage form of claim 1 wherein said medium or high molecular weight polyethylene glycol component comprises PEG 8000.

6. The dosage form of claim 1 wherein said medium or high molecular weight polyethylene glycol comprises PEG 20,000.

7. The dosage form of claim 1 wherein said medium or high molecular weight component is a mixture of medium and high molecular weight polyethylene glycols.

8. The dosage form of claim 7 wherein said mixture of medium and high molecular weight polyethylene glycols is a mixture of PEG 8000 and PEG 20,000.

9. The dosage form of claim 1 wherein said polyethylene oxide has a molecular weight of about 100,000.

10. The dosage form of claim 1 wherein said polyethylene oxide has a molecular weight of about 5,000,000.

11. The dosage form of claim 1 wherein said polyethylene oxide has a molecular weight of about 100,000 and is present in an amount from about 2% to about 10% by weight.

12. The dosage form of claim 1 additionally comprising a plasticizer.

13. The dosage form of claim 12 wherein said plasticizer is propylene glycol.

14. The dosage form of claim 12 wherein said plasticizer is present in a proportion of about 3 percent by weight.

15. The dosage form of claim 1 wherein said pharmaceutical compound is nitroglycerin.

16. The dosage form of claim 1 wherein said pharmaceutical compound is scopolamine.

17. The dosage form of claim 1 wherein said pharmaceutical compound is an estrogen.

18. The dosage form of claim 17 wherein said estrogen is selected from the group consisting of 17-beta-estradiol and ethinylestradiol.

19. The dosage form of claim 17 wherein said estrogen is present in proportion of from about 0.02 percent to about 0.05 percent by weight.

20. The dosage form of claim 1 wherein said pharmaceutical compound is a progestin.

21. The dosage form of claim 20 wherein said progestin is norethindrone.

22. The dosage form of claim 20 wherein said progestin is present in a proportion of from about 1.0 percent to about 5.0 percent by weight.

23. The dosage form of claim 1 wherein said pharmaceutical compound is a mixture of an estrogen and a progestin.

24. The dosage form of claim 33 wherein said estrogen is present in a proportion of from about 0.02 to about 0.05 percent by weight and said progestin is present in a proportion of from about 1.0 percent to about 5.0 percent by weight.

25. The dosage form of claim 23 wherein said estrogen is ethinylestradiol present in a proportion of about 0.02 percent by weight and said progestin is norethindrone present in a proportion of about 2.0 percent by weight.

26. The dosage form of claim 23 wherein said estrogen is 17-beta-estradiol present in a proportion of about 0.2 percent by weight and said progestin is norethindrone present in a proportion of about 2.0 percent by weight.

27. The dosage form of claim 1 wherein said pharmaceutical compound is gonadotropin releasing hormone.

28. The dosage form of claim 1 wherein said pharmaceutical compound is human growth hormone.

29. The dosage form of claim 1 wherein said pharmaceutical compound is insulin.

30. The dosage form of claim 1 wherein said pharmaceutical compound is phenylephrine.

31. The dosage form of claim 1 wherein said pharmaceutical compound is desmopressin.

32. The dosage form of claim 1 wherein said pharmaceutical compound is oxytocin.

33. The dosage form of claim 1 wherein said pharmaceutical compound is vasopressin.

34. The dosage form of claim 1 wherein said pharmaceutical compound is nicotine.

35. The dosage form of claim 1 wherein said pharmaceutical compound is verapamil.

36. The dosage form of claim 1 wherein said pharmaceutical compound is isosorbide dinitrate.

37. The dosage form of claim 1 wherein said pharmaceutical compound is oxymetazoline.

38. The dosage form of claim 1 having the following composition

| | |
|---|---|
| PEG 1450 | 11.0% by weight |
| PEG 3350 | 25.0% by weight |
| PEG 8000 | 59.0% by weight |
| PEO (MW 5,000,000) | 5.0% by weight |

39. The dosage form of claim 1 wherein said dosage form is a buccal dosage form.

40. The dosage form of claim 1 wherein said dosage form is an oral dosage form.

41. The dosage form of claim 1 wherein said dosage form is selected from the group consisting of a lozenge, a lamella, a disk, and a wafer.

42. The dosage form of claim 1 wherein said dosage form is a buccal dosage form having a length of from about 5 mm to about 10 mm, a width of from about 2 mm to about 10 mm and a thickness of from about 0.2 mm to 3 mm.

43. The dosage form of claim 42 wherein said thickness is from about 0.5 mm to about 1.5 mm.

44. The dosage form of claim 1 wherein the total weight of said dosage is from about 10 mg to about 150 mg.

45. The dosage form of claim 1 wherein the total weight of said dosage form is from about 50 mg to about 100 mg.

* * * * *